United States Patent
Vale et al.

(10) Patent No.: US 10,285,763 B2
(45) Date of Patent: May 14, 2019

(54) ACTUATION ELEMENT GUIDE WITH TWISTING CHANNELS

(71) Applicant: Intuitive Surgical Operations, Inc., Sunnyvale, CA (US)

(72) Inventors: Timothy M. Vale, San Jose, CA (US); Daniel Saraliev, Soquel, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 216 days.

(21) Appl. No.: 15/301,140

(22) PCT Filed: Mar. 17, 2015

(86) PCT No.: PCT/US2015/020914
§ 371 (c)(1),
(2) Date: Sep. 30, 2016

(87) PCT Pub. No.: WO2015/153111
PCT Pub. Date: Oct. 8, 2015

(65) Prior Publication Data
US 2017/0020616 A1 Jan. 26, 2017

Related U.S. Application Data

(60) Provisional application No. 62/037,178, filed on Aug. 14, 2014, provisional application No. 61/974,354, filed on Apr. 2, 2014.

(51) Int. Cl.
*A61B 17/00* (2006.01)
*A61B 34/30* (2016.01)

(52) U.S. Cl.
CPC .... *A61B 34/30* (2016.02); *A61B 2017/00526* (2013.01); *A61B 2034/302* (2016.02); *A61B 2034/305* (2016.02)

(58) Field of Classification Search
CPC ......... A61B 34/30; A61B 34/71; A61B 34/70; A61B 2017/00526; A61B 2017/3445;
(Continued)

(56) References Cited

U.S. PATENT DOCUMENTS 7,090,637 B2 8/2006 Danitz et al.
7,666,191 B2 2/2010 Orban, III
(Continued)

FOREIGN PATENT DOCUMENTS

DE 2820239 A1 11/1978
EP 0165718 A2 12/1985
(Continued)

OTHER PUBLICATIONS

International Search Report and Written Opinion for Application No. PCT/US15/20914, dated Jun. 9, 2015, 12 pages.
(Continued)

*Primary Examiner* — Katrina M Stransky
(74) *Attorney, Agent, or Firm* — Jones Robb, PLLC

(57) ABSTRACT

An actuation element guide for a surgical instrument comprises a first piece, a second piece, at least one guide channel defining a twisted path about a longitudinal axis of the guide. The guide channel may be between the inner piece and the outer piece. A cross-section of the at least one guide channel, at a location along an axial length of the guide, may be defined by a surface portion of the first piece and by a surface portion of the second piece. Exemplary embodiments further regard medical devices including an actuation element guide and methods of manufacturing an actuation element guide.

24 Claims, 11 Drawing Sheets

(58) Field of Classification Search
CPC ...... A61B 2017/2947; A61B 2017/291; A61B 2017/2919; A61B 2017/2927; A61B 17/29; A61B 2034/715; A61B 2034/302; A61B 2034/306; A61B 2034/305; A61B 2017/2908

See application file for complete search history.

(56) References Cited

U.S. PATENT DOCUMENTS

| | | | |
|---|---|---|---|
| 7,785,252 B2 | 8/2010 | Danitz et al. | |
| 8,545,515 B2 | 10/2013 | Prisco et al. | |
| 2004/0167595 A1 | 8/2004 | Tuominen | |
| 2005/0015113 A1* | 1/2005 | Baptiste | A61B 17/068 606/205 |
| 2005/0216033 A1 | 9/2005 | Lee et al. | |
| 2006/0041293 A1 | 2/2006 | Mehdizadeh et al. | |
| 2008/0099420 A1 | 5/2008 | Shiue | |
| 2010/0222677 A1* | 9/2010 | Placek | A61B 18/1477 600/439 |
| 2011/0118755 A1 | 5/2011 | Cooper et al. | |
| 2011/0196419 A1* | 8/2011 | Cooper | A61B 18/1445 606/206 |
| 2011/0277579 A1 | 11/2011 | Anderson et al. | |
| 2012/0277762 A1* | 11/2012 | Lathrop | A61B 34/70 606/130 |
| 2013/0184686 A1 | 7/2013 | Sandford et al. | |
| 2013/0325031 A1 | 12/2013 | Schena et al. | |
| 2013/0325033 A1 | 12/2013 | Schena et al. | |

FOREIGN PATENT DOCUMENTS

| | | |
|---|---|---|
| JP | 2011206268 A | 10/2011 |
| WO | WO-2005120326 A2 | 12/2005 |
| WO | WO-2015127231 A1 | 8/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP15773899.8, dated Nov. 7, 2017, 10 pages.

* cited by examiner

ACTUATION ELEMENT GUIDE WITH TWISTING CHANNELS

CROSS-REFERENCE TO RELATED APPLICATIONS

This application is a national stage application of Int'l. App. No. PCT/US2015/020914, filed internationally on Mar. 17, 2015, which claims the benefit of priority to U.S. Provisional Application No. 61/974,354, filed Apr. 2, 2014 and to U.S. Provisional Application No. 62/037,718, filed Aug. 15, 2014, the entire contents of each of which are incorporated by reference herein.

TECHNICAL FIELD

The present disclosure relates to actuation element guides for remotely-actuated instruments, and related systems and methods. In particular, the present disclosure relates to actuation element guides for surgical instruments.

INTRODUCTION

Remotely controlled surgical instruments, including teleoperated surgical instruments (e.g., surgical instruments operated at least in part with computer assistance, such as instruments operated with robotic technology), are often used in minimally invasive medical procedures. During medical procedures, portions of surgical instruments may be moved in one or more directions, such as via teleoperated (remote control) or manual operation. For instance, the surgical instrument may be actuated by a mechanical force transmission mechanism, located at a proximal end of the surgical instrument shaft, to orient, position, and operate an end effector, located at a distal end of the surgical instrument shaft, in a desired location. The surgical instrument may further include a wrist, such as a jointed, articulatable structure, to which the end effector is connected so that the end effector may be oriented relative to the shaft. The surgical instrument may further include one or more electrical or mechanical end effector actuation elements that pass through the surgical instrument, including through the wrist, to actuate the end effector in order to effect a surgical procedure.

International PCT Application No. PCT/US15/16854, filed Feb. 20, 2015, claiming priority to U.S. Patent Application No. 61/943,084, (filed 21 Feb. 2014) (entitled "Mechanical Joints, and Related Systems and Methods"), each of which is hereby incorporated by reference herein in its entirety, describes actuation elements extending along twisted paths. Bending (e.g., articulating) a wrist, which may support an end effector on a shaft, may result in bending of actuation element(s) that control movement of the end effector, which may cause a change in a path length of the end effector actuation element(s). Such a change in length can result in unintended motions and/or actuations of the end effector. In view of this, it is desirable to provide a surgical instrument that includes an actuation element guide to support one or more end effector actuation elements in a manner that substantially conserves a path length of the actuation element(s) when a wrist of the instrument is articulated. Further it is desirable to provide such an actuation element guide that is relatively easy to manufacture.

SUMMARY

Exemplary embodiments of the present disclosure may solve one or more of the above-mentioned problems and/or may demonstrate one or more of the above-mentioned desirable features. Other features and/or advantages will become apparent from the description that follows.

In accordance with at least one exemplary embodiment, an actuation element guide for a surgical instrument comprises a first piece, a second piece, at least one guide channel defining a twisted path about a longitudinal axis of the guide. A cross-section of the at least one guide channel, at a location along an axial length of the guide, is defined by a surface portion of the first piece and by a surface portion of the second piece.

In accordance with at least one exemplary embodiment, a method is directed to manufacturing an actuation element guide for a surgical instrument. The actuation element guide defines at least one guide channel defining a twisted path about a longitudinal axis of the guide. The method comprises assembling a first piece and a second piece together. The assembling the first piece and the second piece together further comprises defining the at least one guide channel such that a cross-section of the at least one guide channel in a plane perpendicular to the longitudinal axis of the guide comprises at least a first surface portion of the first piece and a second surface portion of the second piece.

In accordance with at least one exemplary embodiment, a medical device comprises a shaft comprising a distal end, a surgical end effector comprising a movable component, a flexible actuation element guide, and an actuation element. The flexible actuation element guide comprises an inner piece and an outer piece surrounding the inner piece. The guide is positioned between the distal end of the shaft and the surgical end effector. A guide channel is between the inner piece and the outer piece. The guide channel twists around a longitudinal centerline of the guide. The actuation element comprises a distal end. The actuation element extends through the guide channel. The distal end of the actuation element is mechanically coupled to the movable component of the end effector.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
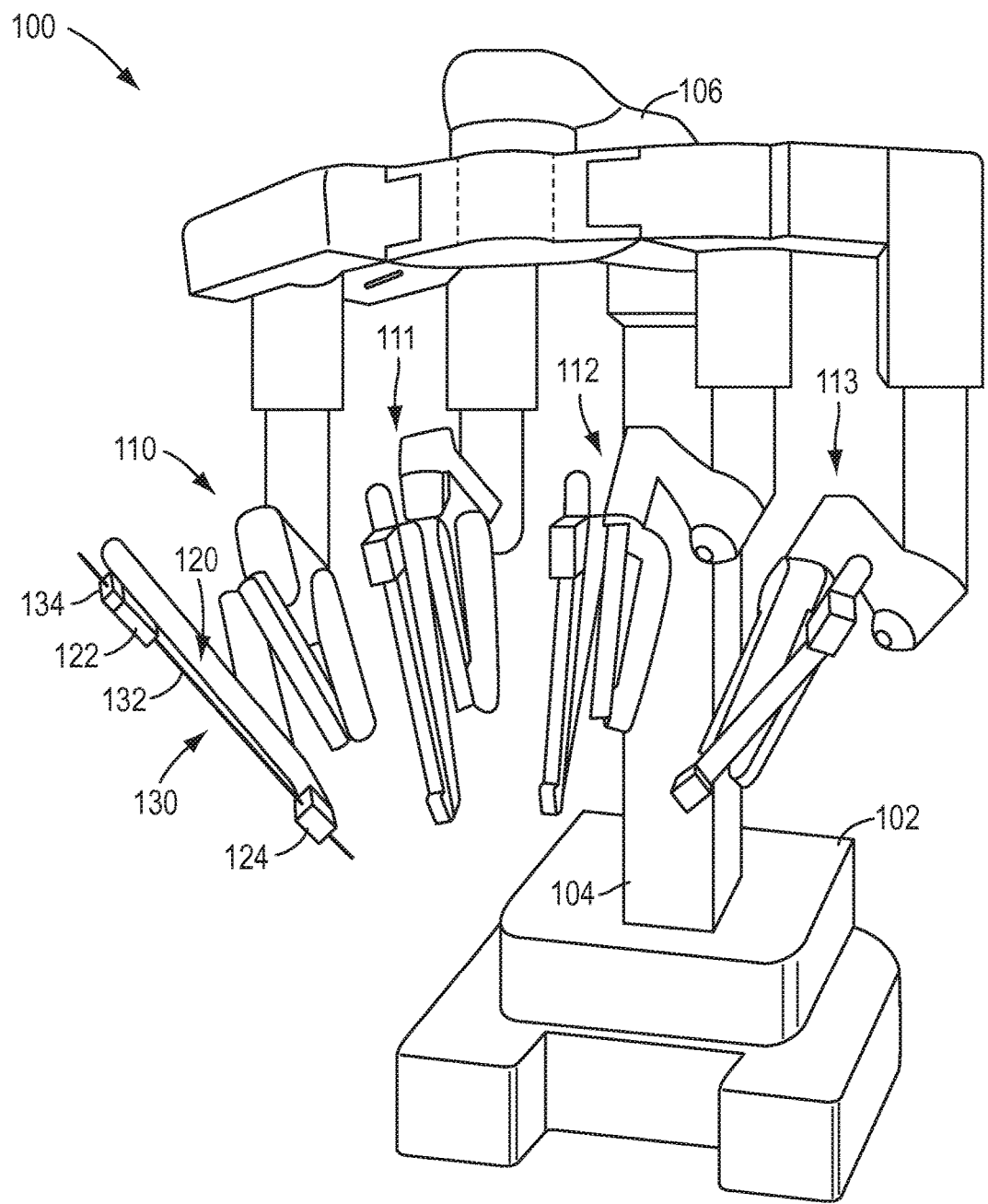
FIG. 1 shows a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates actuation element guides (e.g., actuation element supports) that include a first piece, a second piece, and one or more guide channels. For example, the first piece is an inner piece and the second piece is an outer piece that surrounds the first piece. A cross-section of a guide channel, at a location along an axial length of the guide, is defined by at least surface portions of the first piece and the second piece, according to an exemplary embodiment. According to various exemplary embodiments, assembling an actuation element guide from at least two pieces facilitates manufacture of the actuation element guide in a more efficient manner, such as by permitting more efficient manufacturing processes to be used to manufacture the pieces from which the guide is assembled.

In accordance with various exemplary embodiments, a guide channel defines a twisted path about a longitudinal axis of the guide. The twisted path guides and/or supports a mechanical actuation element extending along the channel such that a path length of the actuation element does not substantially change, such as when the guide is bent, in accordance with various exemplary embodiments. Surfaces of at least the first piece and the second piece cooperate to define channel along at least a portion of the twisted path. According to an exemplary embodiment, surface of one of the first piece and the second piece include radially extending projections that extend between the first piece and the second piece. The projections have a spoke-like configuration, according to an exemplary embodiment. In one example, the second piece surrounds the first piece and the projections radially extend from an inner surface of the second piece and contact an outer surface of first piece. The first piece can have grooves to receive ends of the projections radially extending from the inner surface of the second piece. The first piece can have cylindrical cross-section. In another example, the second piece surrounds first piece and the projections extend from an outer surface of the first piece and contact an inner surface of the second piece. The second piece can have grooves to receive ends of the projections. The second piece can have cylindrical cross-section. In accordance with at least one exemplary embodiment, an actuation element guide includes a cutout to facilitate bending of the actuation element guide. According to an exemplary embodiment, the cutout is a recess located in an outer radial surface of the actuation element guide.

According to various exemplary embodiments, an actuation element guide includes a first portion and a second portion disposed in an end-to-end manner along a longitudinal proximal-distal direction of the guide, according to an exemplary embodiment. For example, the first portion includes longitudinally straight guide channels and the second portion includes twisted channels with respect to the longitudinal axis of the guide, wherein the second portion includes the first piece and the second piece of the actuation element guide. According to an exemplary embodiment, the first portion is disposed within an instrument where bending is minimal or does not occur (e.g., a shaft of an instrument) while the second portion is disposed within an instrument where bending occurs (e.g., a wrist of an instrument). According to an exemplary embodiment, the actuation element guide includes one or more port openings disposed in a lateral side of the actuation element guide. A port opening provides access to an interior region of the actuation element guide. An actuation element extends within the interior region of the actuation element guide, exit the actuation element guide via the port opening, and extend extends along at least a portion of an instrument shaft outside of the actuation element guide, according to an exemplary embodiment.

In accordance with at least one exemplary embodiment, a method of manufacturing an actuation element guide for a surgical instrument includes assembling a first piece and a second piece together. According to an exemplary embodiment, each of the first piece and the second piece is formed via, for example, molding, extruding or another technique. The assembling of the first piece and the second piece includes assembling the first and second pieces together so that surface portions of the first piece and second piece define a cross section of at least one channel defining a twisted path about a longitudinal axis of the guide. According to an exemplary embodiment, the first and second pieces are joined to one another. Joining the first piece and the second piece includes laser welding, according to an exemplary embodiment. According to an exemplary embodiment, joining the first piece and the second piece includes inserting the first piece within the second piece, wherein the second piece includes a transparent or translucent material configured to transmit energy from a laser through the second piece to the first piece.

Referring now to FIG. 1, an exemplary embodiment of a patient side cart 100 of a teleoperated surgical system is shown. A teleoperated surgical system can further include a surgeon console (not shown) for receiving input from a user to control instruments mounted at patient side cart 100. A teleoperated surgical system also can include an auxiliary equipment/vision cart (not shown), which can optionally include at least part of the system's computer control equipment, as described in, for example, U.S. Patent Application Pub. No. US 2013/0325033 A1, entitled "Multi-Port Surgical Robotic System Architecture" and published on Dec. 5, 2013, and U.S. Patent Application Pub. No. US 2013/0325031 A1, entitled "Redundant Axis and Degree of Freedom for Hardware-Constrained Remote Center Robotic Manipulator" and published on Dec. 5, 2013, each of which is hereby incorporated by reference in its entirety. Further, the exemplary embodiments described herein may be used, for example, with a da Vinci® Surgical System, such as the da Vinci Si® Surgical System, or the da Vinci Xi® Surgical System, both with or without Single-Site® single orifice surgery technology, all commercialized by Intuitive Surgical, Inc.

Patient side cart 100 includes a base 102, a main column 104, and a main boom 106 connected to main column 104. Patient side cart 100 may also include a plurality of teleoperated manipulator arms 110, 111, 112, 113, which are each connected to main boom 106, according to an exemplary embodiment. Manipulator arms 110, 111, 112, 113 may each include an instrument mount portion 120 to which an instrument 130 may be mounted, which is illustrated as being attached to manipulator arm 110. Portions of manipulator arms 110, 111, 112, 113 are manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may include an actuation interface assembly 122 and a cannula mount 124. A shaft 132 of instrument 130 extends through cannula mount 124 and on to a surgery site during a surgical procedure. A force transmission mechanism 134 of instrument 130 is mechanically coupled with the actuation interface assembly 122, according to an exemplary embodiment. Cannula mount 124 is configured to hold a cannula (not shown) through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 130, as those skilled in the art are familiar with.

Although the exemplary embodiment of FIG. 1 shows an instrument 130 attached to only manipulator arm 110 for ease of illustration, an instrument may be attached to any and each of manipulator arms 110, 111, 112, 113. An instrument 130 may be a surgical instrument with an end effector or may be an endoscopic imaging instrument or other sensing instrument utilized during a surgical procedure to provide information (e.g., visualization, electrophysiological activity, pressure, fluid flow, and/or other sensed data) of a remote surgical site. In the exemplary embodiment of FIG. 1, a surgical instrument with an end effector or an imaging instrument may be attached to and used with any of manipulator arms 110, 111, 112, 113. However, the embodiments described herein are not limited to the exemplary embodiment of the patient side cart of FIG. 1, and various other teleoperated surgical system configurations, including patient side cart configurations, may be used with the exemplary embodiments described herein.

Figure 2:
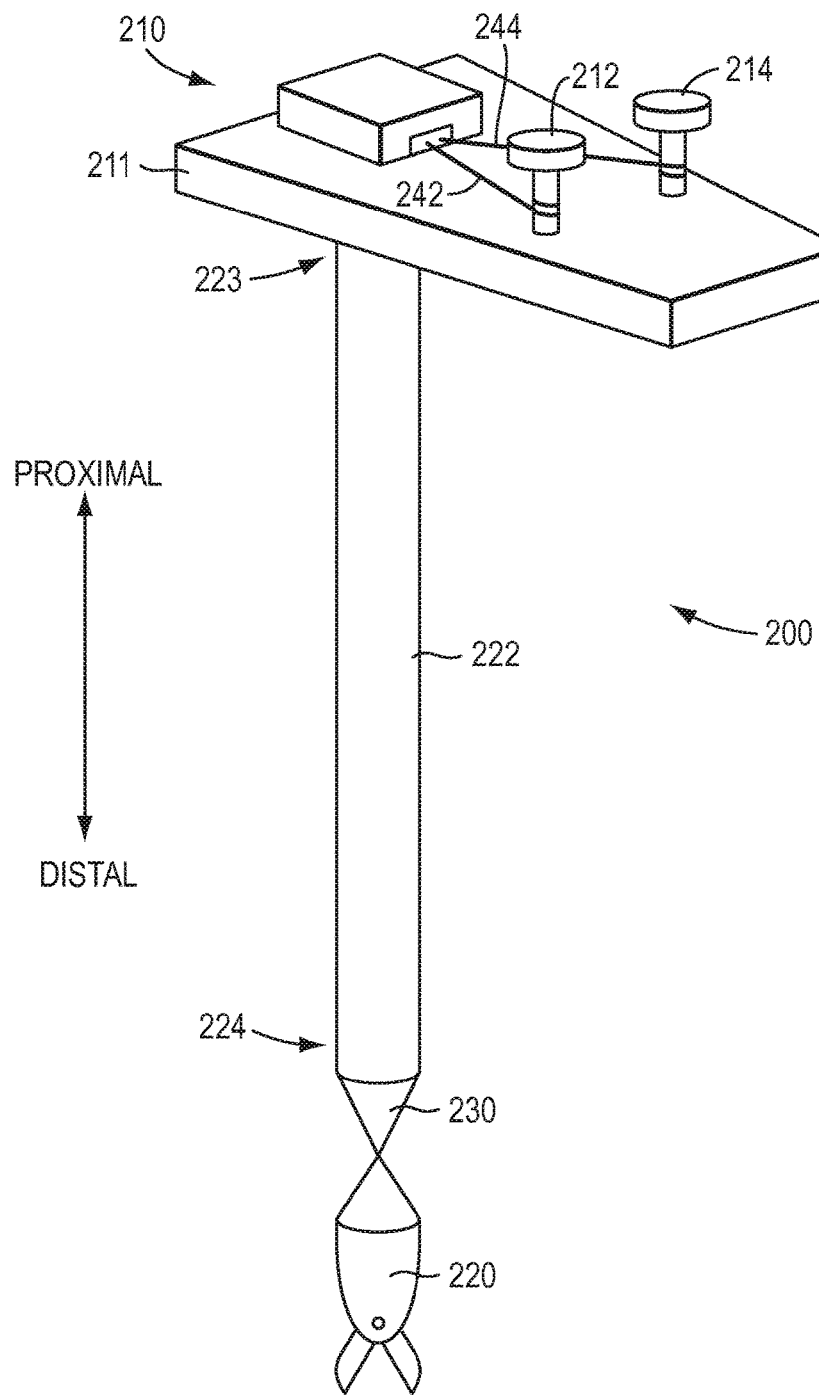
FIG. 2 shows a diagrammatic side view of a surgical instrument for a teleoperated surgical system, according to an exemplary embodiment.

Turning to FIG. 2, a schematic side view of an exemplary embodiment of a surgical instrument 200 is shown. For instance, surgical instrument 200 is used as instrument 130 with the patient side cart 100 of the exemplary embodiment of FIG. 1. Surgical instrument 200 includes a force transmission mechanism 210 (a chassis 211 which is shown in the exemplary embodiment of FIG. 2, with a housing not being shown to reveal components of the force transmission mechanism 210 within), a shaft 222 connected to force transmission mechanism 210 at a proximal end 223 of shaft 222, a wrist 230 connected to a distal end 224 of shaft 222, and an end effector 220 connected to wrist 230, according to an exemplary embodiment. According to an exemplary embodiment, shaft 222 is flexible. Various diameters for shaft 222 may exist in a range suitable for minimally invasive surgery. According to an exemplary embodiment, shaft 222 has a diameter ranging from about 3 mm to about 15 mm. For example, shaft 222 has a diameter of 3 mm, 5 mm, 8 mm, 13 mm, or 15 mm. According to another exemplary embodiment, the diameter of shaft 222 ranges, for example, from about 5 mm to about 8 mm.

Surgical instrument 200 may include one or more members to transmit force between force transmission mechanism 210 and end effector 220 and/or between force transmission mechanism 210 and wrist 230. For example, actuation elements 242, 244 connect force transmission mechanism 210 to end effector 220 to provide actuation forces to end effector 220, such as by extending through an interior of shaft 222. By using actuation elements 242, 244, force transmission mechanism 210 actuates end effector 220 to control, for example, a jaw of end effector 220 (or other moveable part of end effector 220). In another example, actuation elements 242, 244 are used to actuate wrist 230 in one or more orientation degrees of freedom (e.g. pitch and/or yaw). Actuation elements 242, 244 may be tension elements, such as when force transmission mechanism 210 is a pull-pull mechanism, or one or more actuation element rods or push rods, such as when force transmission mechanism 110 is a push-pull mechanism, as described in U.S. Pat. No. 8,545,515 (issued Oct. 1, 2013), which is hereby incorporated by reference in its entirety.

Force transmission mechanism 210 may include one or more components to engage with a patient side cart of a teleoperated surgical system to transmit a force provided by patient side cart to surgical instrument 100. Persons skilled in the art will be familiar with surgical instrument force transmission mechanisms, which receive a mechanical input force from a power source (e.g., an electric motor from a manipulator supporting the instrument) and convert and/or redirect the received force to an output force to drive a component (e.g., a wrist, and end effector) on the instrument. For example, force transmission mechanism 210 connects with the actuation interface assembly 122 of the patient side cart 100 of the exemplary embodiment of FIG. 1 so actuation interface assembly 122 transmits forces to force transmission mechanism 210 to actuate instrument 200. According to an exemplary embodiment, force transmission mechanism 210 includes one or more actuation input mechanisms 212, 214 that engage (e.g., via a distal end of force transmission mechanism 210) with a manipulator of a patient side cart, such as actuation interface assembly 122 of patient side cart 100. When force transmission mechanism 210 is a pull-pull mechanism and actuation elements 242, 244 are tension elements, actuation input mechanisms 212, 214 are capstans that are rotationally driven by actuation interface assembly 122 to tension actuation elements 242, 244 to actuate instrument, according to an exemplary embodiment. Thus, actuation input mechanisms 212, 214 utilize actuation forces from an actuation interface assembly to actuate instrument 200. Force transmission mechanism 210 may include other actuation input mechanisms to actuate various other functionalities of a surgical instrument, as those having ordinary skill in the art are familiar with.

Figure 3:
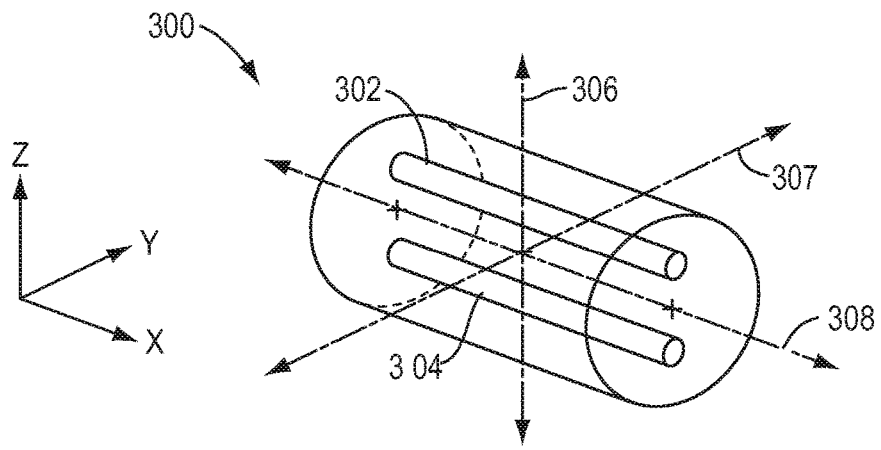
FIG. 3 shows a diagrammatic perspective view of a single flexible and bendable member in a straight configuration, according to an exemplary embodiment.
Figure 4:
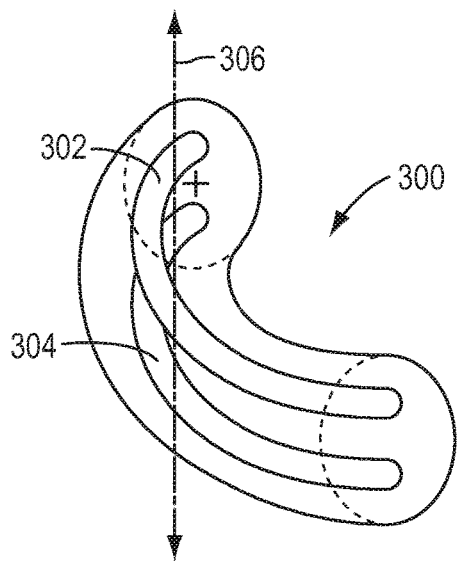
FIG. 4 shows the member of FIG. 3 in a bent configuration.

Bending may have an effect upon actuation elements when the actuation elements pass through bent portions of a surgical instrument. For instance, bending wrist 230 of instrument 200 of the exemplary embodiment of FIG. 2 may have an effect upon actuation elements 242, 244, such as when actuation elements 242, 244 extend through wrist 230 to end effector 220. For illustrative purposes, FIG. 3 is an illustrative schematic perspective view of a single flexible member 300 that can bend, with axes 306, 307 indicating directions of bending, similar to how a wrist of a surgical instrument is bent. A first actuation element 302 and a second actuation element 304 extend through member 300, such as along a longitudinal axis 308 of member 300. In the exemplary embodiment of FIG. 3, wherein member 300 is in a straight (neutral) configuration, an axis 306 passes through each of first actuation element 302 and second actuation element 304, such as along the Z axis in the exemplary embodiment of FIG. 3. As shown in FIG. 4, when member 300 is bent, with axis 306 indicating a direction member 300 is bent in, first and second actuation elements 302, 304 bend as well. There is no relative change in path length between first actuation element 302 and second actuation element 304 because actuation element 302, 304 are bent in the same manner. According to an exemplary embodiment, the path length of actuation elements 302, 304 is the length each element 302, 304 traverses from one end of member 300 to another. For example, each of actuation elements 302, 304 is fixed relative to member 300 and a length of each actuation element 302, 304 does not change but the path an actuation element 302, 304 traverses along member 300 may change when member 300 is bent. Thus, when member 300 is bent, a path of one of actuation elements 302, 304 along member 300 does not become substantially longer or substantially shorter than the path of the other.

Figure 5:
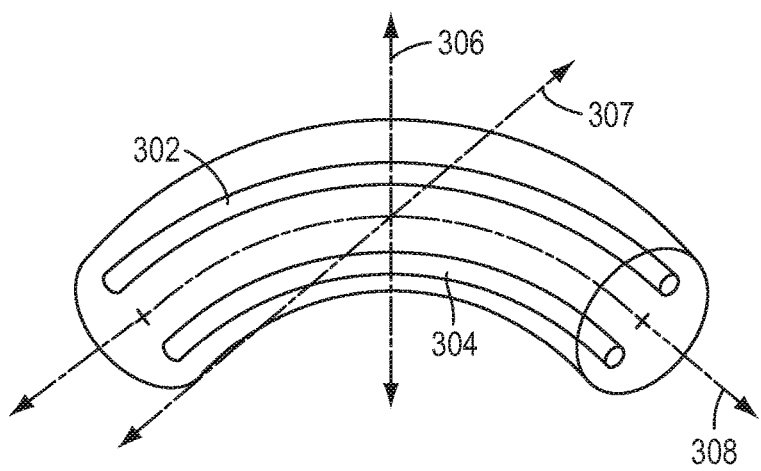
FIG. 5 shows the member of FIG. 3 in a bent configuration.

Referring again to FIG. 3, a second axis 307 for member 300 passes between first actuation element 302 and second actuation element 204, such as along the Y axis in the exemplary embodiment of FIG. 3. When member 300 is bent in the manner shown in FIG. 5, with axis 307 indicating a direction of bending, first actuation element 302 is stretched relative to its neutral position, causing a positive change in a length of its path along member 300, while second actuation element 304 is compressed relative to its neutral position, causing a negative change in a length of its path along member 300. Therefore, bending member 300 in the manner shown in the exemplary embodiment of FIG. 5 can cause a change in the relative path lengths of actuation elements 302, 304, with one actuation element becoming longer the other. Such a relative change in path length can interfere with the function of actuation elements, such as to actuate an end effector. For instance, when actuation elements 302, 304 are used to open and close an end effector by applying tension to actuation elements 302, 304, similar to actuation elements 242, 244 of the exemplary embodiment of FIG. 2 (e.g., so that ends of actuation elements 302, 304 are fixed to the end effector and a force transmission mechanism, such as actuation input mechanisms 212, 214 of FIG. 2), a relative change in path length between actuation elements 302, 304 may create tension, which may result in actuation of the end effector, or may create slack in one of the actuation elements 302, 304, diminishing the ability of the actuation element to transmit the desired tension and cause a desired actuation of an end effector.

It may be desirable to design a joint of a surgical instrument to minimize relative changes in path lengths of actuation elements extending through the joint. For instance, a single actuation element is provided to actuate an end effector, with the single actuation element extending along a centerline of a surgical instrument. In such a configuration, axes defining directions of bending are substantially orthogonal to one another (e.g., axes 306, 307 in the exemplary embodiment of FIG. 3), such as to provide two degrees of freedom for bending a surgical instrument, and pass through the center of the instrument and the actuation element. As a result, the path length of the single actuation element does not substantially change when the surgical instrument is bent. However, although this approach can be useful when a single actuation element is sufficient to control an end effector, a surgical instrument may include multiple actuation elements, such as to actuate different components of the instrument, including an end effector and a wrist of an instrument, among others. In view of these considerations, it is desirable to extend actuation elements along a twisted path to substantially conserve the path lengths of actuation elements that are positioned off a neutral axis. For example, actuation elements extend along twisted paths according to the various exemplary embodiments described in International PCT Application No. PCT/US15/16854, filed Feb. 20, 2015, claiming priority U.S. Patent Application No. 61/943,084 (filed Feb. 21, 2014) (entitled "Mechanical Joints, and Related Systems and Methods"), each being incorporated by reference herein in its entirety.

Various exemplary embodiments contemplate one or more structures that guide one or more actuation elements along a twisted path, as described in the exemplary embodiments noted above. One or more structures may provide support to an actuation element and guide the actuation element along its length, such as to minimize or reduce buckling of the actuation element as the actuation element extends along the twisted path according to the exemplary embodiments noted above.

Figure 6:
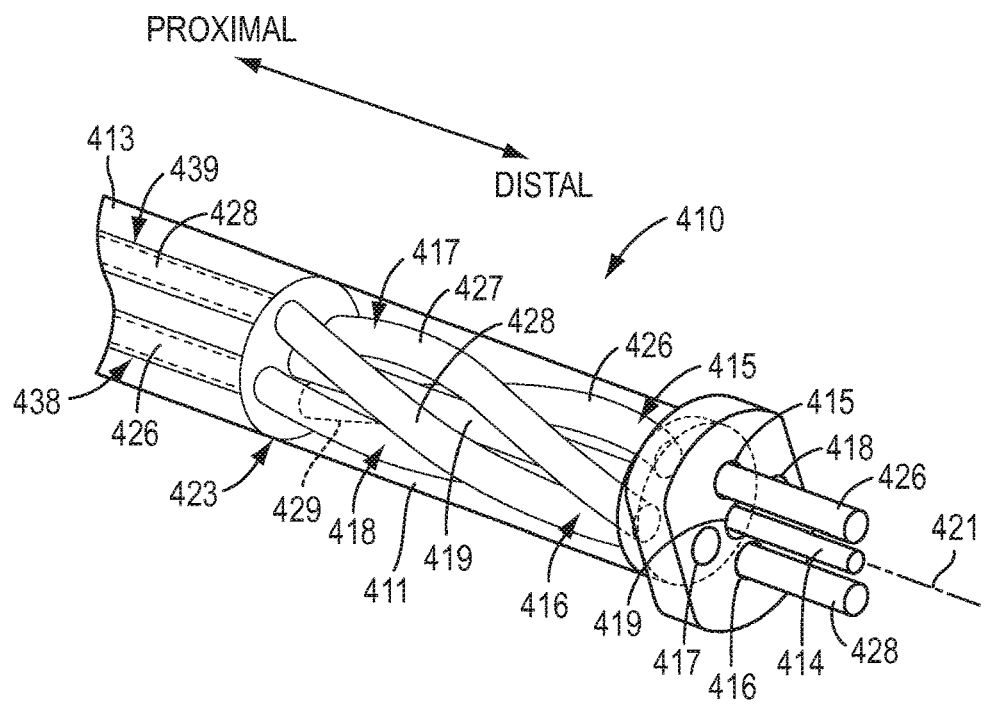
FIG. 6 shows a perspective view of a distal portion of a surgical instrument shaft including an actuation element guide, according to an exemplary embodiment.

FIG. 6 shows a distal portion of a surgical instrument that includes an actuation element guide 410 (e.g., actuation element support) located at a distal end of an instrument shaft, such as at distal end 224 of shaft 222 in the exemplary embodiment of FIG. 2. According to an exemplary embodiment, a first portion 411 of actuation element guide 410 includes twisted passages 415, 416 that provide a twisted path for actuation elements 426, 428 that extend through passages 415, 416 of first portion 411. Actuation elements 426, 428 extend out of a proximal end 423 of first portion 411 and into a second portion 413 of actuation element guide 410, according to an exemplary embodiment. Second portion 413 includes substantially straight passages 438, 439 through which actuation elements 426, 428 extend, as shown in the exemplary embodiment of FIG. 6. Although only two passages 438, 439 are depicted within section portion 413 in the exemplary embodiment of FIG. 6 for ease of illustration, second portion 413 of actuation element guide 410 includes the same number of passages as first portion 411, according to an exemplary embodiment. According to an exemplary embodiment, the passages of second portion 413 are joined to the passages of first portion 411 so that any actuation elements extending through the passages of second portion 413 extend through corresponding passages in first portion 411.

According to various exemplary embodiments, actuation element guide 410 includes various numbers of passages to provide a twisted path for one or more actuation elements. For instance, actuation element guide 410 may include one passage, two passages, three passages, or four or more passages. For instance, actuation element guide 410 may include a third passage 417 and a fourth passage 418, which may be used for additional actuation elements or for flux conduits 427, 429, such as electrical conductors to provide electrical energy to an end effector (not shown).

According to an exemplary embodiment, guide 410 further includes a central passage 419 through which an actuation element 414 extends. Central passage 419 extends along a longitudinal centerline 421 of an instrument including guide 410 so that any member extending through central passage 419, such as actuation element 414 or a flux conduit, does not experience a substantial change in path length when guide 410 is bent, according to an exemplary embodiment. Centerline 421 is also a centerline of guide 410, according to an exemplary embodiment. Actuation element 414 is used, for example, to actuate an end effector or component of an end effector, such as a cutting blade in an exemplary embodiment.

The actuation elements of the various exemplary embodiments described herein that are radially offset from a neutral axis or centerline (e.g., centerline 412 in FIG. 6) may be used to actuate various instrument components. For example, the actuation elements of the various exemplary embodiments described herein that are radially offset from a neutral axis or centerline actuate a wrist distal to actuation element guide 410. In another example, the actuation elements are radially offset from a neutral axis or centerline and actuate another instrument component than a wrist. For instance, actuation element 414 is used to actuate an end effector, while actuation elements 426, 428 are used to actuate the wrist that end effector is connected to. According to another example, a flux conduit extends through central passage 419 instead of actuation element 414.

In contrast to passages 415-418, central passage is located along the longitudinal centerline 421 of an instrument, as shown in FIG. 6, according to an exemplary embodiment. Because central passage 419 is located along longitudinal centerline 421, actuation elements 426, 428 and their respective passages 415, 416 are radially offset from centerline 421. Thus, when a wrist is actuated to bend an instrument, actuation elements 426, 428 could experience a change in path length, without measures to minimize or prevent the change in path length. However, guide 410 imparts a twisted path to actuation elements 426, 428 within first portion 411 (such as according to the exemplary embodiments of International PCT Application No. PCT/US15/16854, filed Feb. 20, 2015, claiming priority U.S. Provisional Application No. 61/943,084, (entitled "Mechanical Joints, and Related Systems and Methods"), filed on Feb. 21, 2014, each being incorporated by reference herein in its entirety) so that actuation elements 426, 428 do not experience a substantial change in path length over the length of a wrist.

According to an exemplary embodiment, an actuation element guide is positioned in a surgical instrument (e.g., wrist 230 in FIG. 2) so that the location of the guide corresponds to the location of a wrist because the wrist can bend, which could cause actuation elements extending through the wrist to change in path length. For example, first portion 411 of guide 410, which includes twisted passages 415-418, is positioned within a wrist of an instrument (e.g., wrist 230 of the exemplary embodiment of FIG. 2) and second portion 413 of guide 410, which includes straight passages, is positioned within a shaft of an instrument proximal to the wrist (e.g., shaft 222 of the exemplary embodiment of FIG. 2). Thus, twisted passages 415-418 of first portion 411 provide a twisted path so actuation elements extending through passages 415-418 (which is used to actuate, for example, an end effector or the wrist) do not experience a substantial change in path length, such as when the wrist is articulated. Further, because passages 438, 439 of second portion 413 are located within the shaft and do not experience a significant amount of bending, passages 438, 439 are straight, according to an exemplary embodiment.

Figure 7:
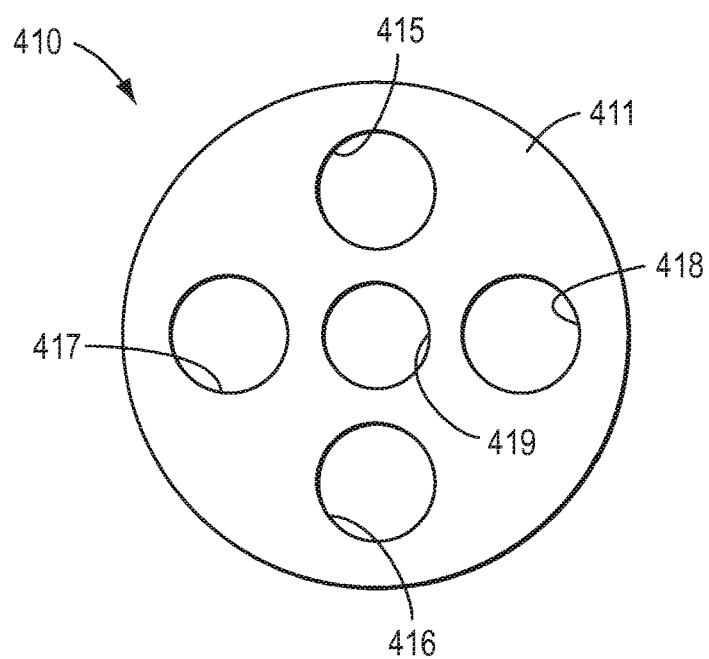
FIG. 7 is an elevation cross-sectional view of the actuation element guide of FIG. 6.

As shown in the exemplary embodiment of FIG. 6 and FIG. 7 (which is a transverse cross-sectional view of guide 410 of FIG. 6), actuation element guide 410 has a solid, single-piece construction with passages 415-419 formed through the length of guide 410. According to an exemplary embodiment, actuation element guide 410 is manufactured, for example, by extruding a polymer material into a substantially cylindrical shape or by molding guide 410. Twisted passages 415-418 are formed through the length of the polymer material by heat forming the extruded material into a twisted shape, such as the shape of first portion 411 in the exemplary embodiment of FIG. 6, according to an exemplary embodiment. Thus, guide 410 may guide one or more actuation elements along a twisted path to substantially conserve the path length of the actuation element(s) and to provide support to the actuation element(s) so buckling of the actuation elements is minimized or prevented.

In various exemplary embodiments, guide 410 is flexible to promote bending of guide 410 when a wrist that guide 410 extends through is actuated. Guide 410 is made from, for example, a polymer material to provide a relatively low coefficient of friction. According to an exemplary embodiment, guide 410 is made of, for example, polyether block amide (PEBAX), fluorinated ethylene propylene (FEP), and other polymer materials having a relatively low coefficient of friction, including elastomers, familiar to one of ordinary skill in the art.

As discussed above with regard to the exemplary embodiment of FIGS. 6 and 7, an actuation element guide may have a single-piece construction. For instance, the guide is a single piece that has been extruded and shaped to include at least a portion with twisted passages. Although such an actuation element guide may be effective for supporting one or more actuation element(s) along a twisted path, it may be desirable to provide an actuation element guide that facilitates manufacture and is still effective to support one or more actuation element(s) along a twisted path. Therefore, other manufacturing methods may be utilized to provide a guide having one or more twisted passages radially offset from and twisting about a centerline of a guide.

Figure 8:
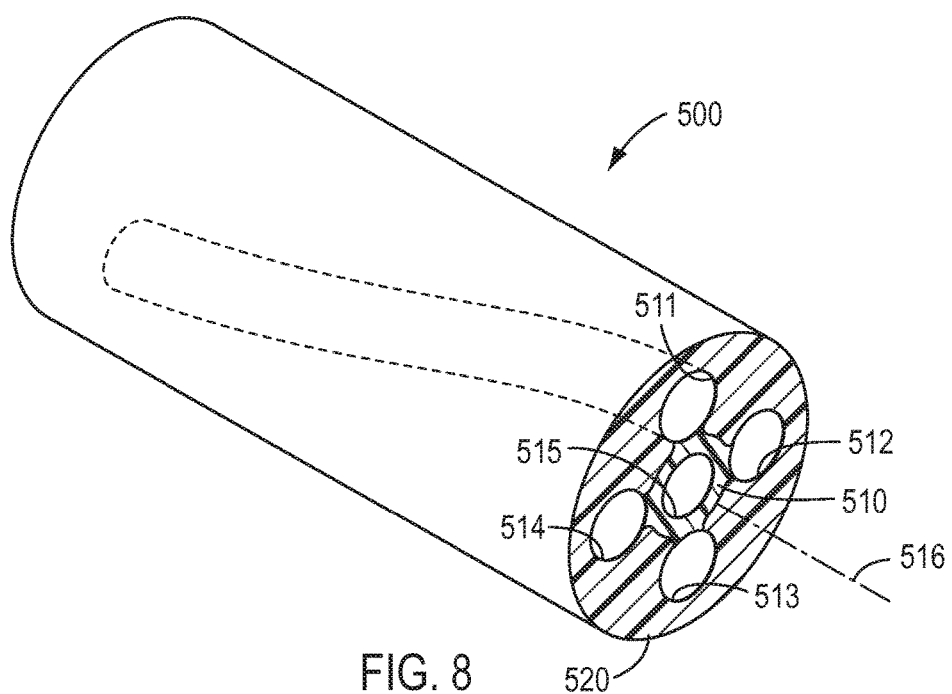
FIG. 8 is a perspective cross-sectional view of an actuation element guide comprising a plurality of pieces, according to an exemplary embodiment.

According to an exemplary embodiment, an actuation element guide is manufactured by joining two or more separate pieces together to form the actuation element guide. Turning to FIG. 8, an exemplary embodiment of an actuation element guide 500 is shown, according to an exemplary embodiment. Actuation element guide 500 includes a plurality of channels 511-515, according to an exemplary embodiment. Channel 515 may be a substantially straight channel that extends along a longitudinal centerline 516 of guide 500 (which may also be the centerline of an instrument including guide 500), similar to passage 419 of the exemplary embodiment of FIG. 6.

According to an exemplary embodiment, channels 511-514 impart a twisted path to actuation elements (not shown) that extend through channels 511-514 (such as according to the exemplary embodiments of International PCT Application No. PCT/US15/16854, filed Feb. 20, 2015, claiming priority U.S. Provisional Application No. 61/943,084, (entitled "Mechanical Joints, and Related Systems and Methods"), filed on Feb. 21, 2014, each incorporated by reference herein in its entirety). For example, channels 511-514 are twisted in a manner similar to passages 415-418 of the exemplary embodiment of FIG. 6, so that the actuation elements within channels 511-514 do not experience a substantial change in path length over the length of a wrist and are supported to minimize or prevent buckling of the actuation elements.

Figure 9:
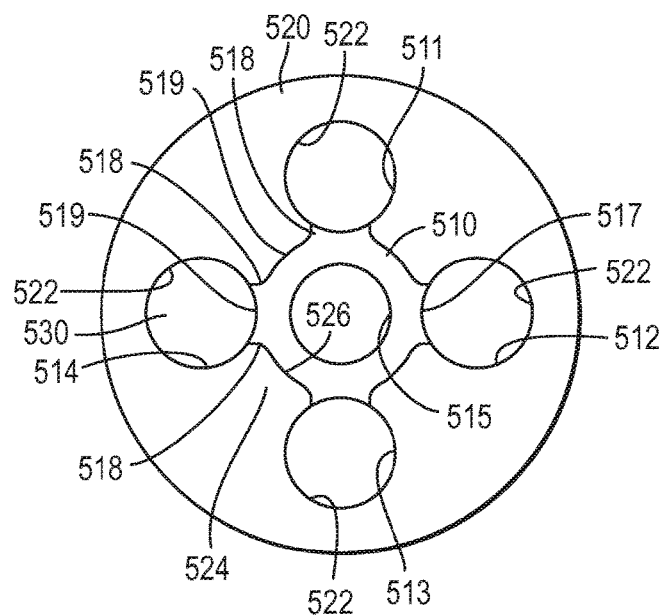
FIG. 9 is an elevation cross-sectional view of the actuation element guide of FIG. 8.

Actuation element guide 500 may have a multi-piece construction comprising an inner piece 510 and an outer piece 520, as shown in the exemplary embodiment of FIG. 8. Inner pieces and outer pieces of the various exemplary embodiments described herein, such as inner piece 510 and outer piece 520, may be first and second pieces of an actuation element guide. According to an exemplary embodiment, inner piece 510 is inserted within outer piece 520, with surfaces of inner piece 510 and outer piece 520 cooperating to define one or more of channels 511-514. As shown in FIG. 9, which is an end view of FIG. 8, outer piece 520 may surround inner piece 510, such as in a concentric manner.

One of the first and second pieces of an actuation element guide includes projections that extend along radial directions of the actuation element guide, according to an exemplary embodiment. The projections of the first or second piece may cooperate with a surface of the other of the first and second piece so that open regions between the projections define twisted channels of an actuation element guide. According to an exemplary embodiment, one of the first and second pieces of an actuation element guide includes projections arranged in a spoke-like configuration, extending either radially outwardly from an inner portion of the first or second piece or extending radially inwardly from an outer portion of the first or second piece. The projections cooperate with a surface of the other of the first and second piece so that open regions between the projections form at least part of the twisted channels of an actuation element guide.

Figure 10:
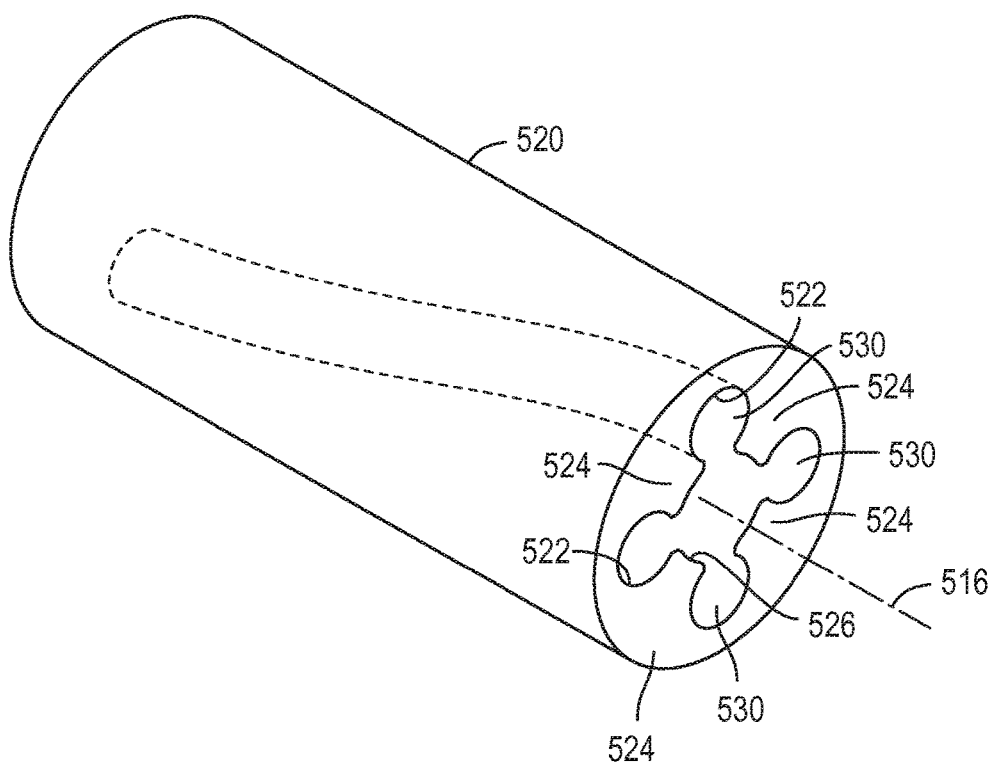
FIG. 10 is a perspective view of the outer piece of the actuation element guide of FIG. 8.

As shown in the exemplary embodiment of FIG. 9 and FIG. 10, which is a perspective view of outer piece 520 with inner piece 510 removed, outer piece 520 has an inner surface 522 that includes one or more projections 524 that project radially inward toward central channel 515 and longitudinal centerline 516. According to an exemplary embodiment, projections 524 and open regions 530 between projections 524 define a spoke-like configuration of outer piece 520. According to an exemplary embodiment, projections 524 of outer piece 520 twist about a longitudinal centerline 516 of actuation element guide 500. Inner surface 522 of outer piece 520 also twist about longitudinal centerline 516 so that open regions 530 twist about longitudinal centerline 516, as shown in the exemplary embodiment of FIG. 10 (with the twisted shape of one open region 530 being depicted in FIG. 10 with dashed lines for ease of viewing), according to an exemplary embodiment. As a result, channels 511-514 (which may be defined, for example, by inner surface 522 and open regions 530 of outer piece 520 and outer surface 517 of inner piece 510), twist about longitudinal centerline 516 along an axial direction of guide 500, as shown in the exemplary embodiment of FIG. 8 (with the twisted shape of only channel 511 being depicted with dashed lines for ease of viewing). According to an exemplary embodiment, a cross section of the twisting channels 511-514 taken at a location along the axial length of guide 500 (e.g., transverse to axis 516) includes surface portions of both the inner piece 510 and the outer piece 520, in particular, an interior surface portion of outer piece 520 and an exterior surface portion of inner piece 510.

Figure 11:
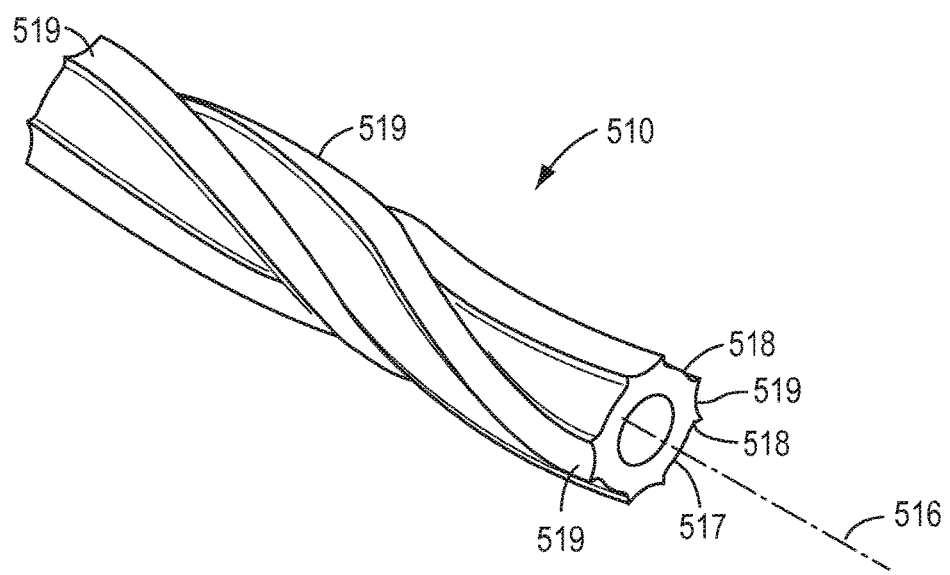
FIG. 11 is a perspective view of the inner piece of the actuation element guide of FIG. 8.

As shown in the exemplary embodiment of FIG. 11, which is a perspective view of inner piece 510 of FIG. 9, inner piece 510 is a modified tube with an outer wall 512 twisted about longitudinal centerline 516 of guide 500. For instance, outer wall 517 of inner piece 510 includes grooves 519 that longitudinally twist about longitudinal centerline 516 of guide 500. Outer wall 512 of inner piece 510 is shaped to mate with corresponding inner ends 526 of projections 524 of outer piece 520, as shown in the exemplary embodiment of FIG. 9. For instance, grooves 519 respectfully receive ends 526 of projections 524 of outer piece 520. Raised portions 518 on either side of a groove 519 further conform the outer wall 517 to projections 524 so that cross-sectional shapes of channels 511-514, as formed by inner surface 522 of outer piece 520 and outer wall 517 of inner piece 510, are continuous or near-continuous circles, according to an exemplary embodiment. Thus, a space defined by inner wall of 522 of outer piece 520, including a space between adjacent projections 524 of outer piece 520, and defined by outer wall 517 of inner piece 510, including a space defined by groove 519, may define one of channels 511-514. Although four twisted channels 511-514 are shown in the exemplary embodiment of FIGS. 8-11, more or fewer channels 511-514 may be formed in guide 500 by using more or fewer projections 524 and grooves 519. Further, although projections 524 and grooves 519 are equally spaced around the longitudinal centerline 516 of guide 500, projections 524 and grooves 519 may be spaced by different distances to provide channels of different sizes.

Figure 12:
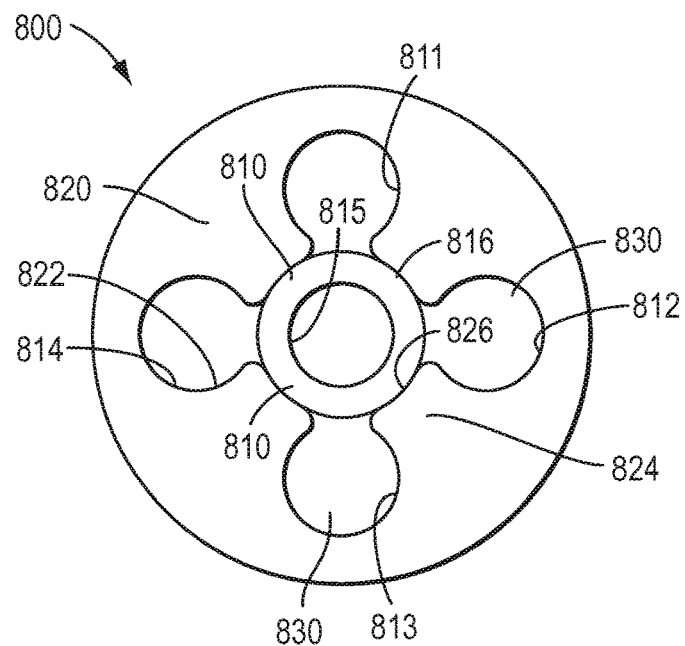
FIG. 12 is an end view of an actuation element guide, according to another exemplary embodiment.

Another exemplary embodiment of an actuation element guide 800 that includes an inner piece 810 and an outer piece 820 is shown in FIG. 12. Inner piece 810 and outer piece 820 may be referred to as first and second pieces. As shown in the exemplary embodiment of FIG. 12, inner piece 810 is a tube structure and outer piece 820 surrounds inner piece 810, such as in a concentric manner. For instance, inner piece 810 is a tube with a generally cylindrical cross-section having a generally uniform wall thickness. As a result, inner piece 810 may be manufactured using a straightforward extrusion technique, although other techniques also may be used. The lumen of the tube of inner piece 810 may form a non-twisting central channel 815.

Outer piece 820 includes an inner surface 822 that includes projections 824 extending radially inward towards central channel 815, according to an exemplary embodiment. Projections 824 and open regions 830 between projections 824 define a spoke-like structure for outer piece 820, according to an exemplary embodiment. Projections 824 and open regions 824 may be twisted along an axial direction of guide 800 (e.g., into and out of the page of FIG. 12, similar to the exemplary embodiment of FIG. 10). According to an exemplary embodiment, outer piece 820 and inner piece 810 contact one another and define twisting channels 811-814 of guide 800. According to an exemplary embodiment, inner ends 826 of projections 824 contact an outer wall 816 of inner piece 810. Thus, open regions 830, projections 824, and outer wall 816 of inner piece 810 cooperate to define twisting channels 811-814 along an axial length of guide 800, similar to the exemplary embodiment of FIG. 8. As a result, inner piece 810 and outer piece 820 may define twisting channels 811-814 at a point (e.g., cross-section) along the axial length of guide 800. According to an exemplary embodiment, a cross section of the twisting channels 811-814 taken at a location along the axial length of guide 800 (e.g., transverse to a longitudinal axis of actuation element guide 800) includes surface portions of both the inner piece 810 and the outer piece 820, in particular, an interior surface portion of outer piece 820 and an exterior surface portion of inner piece 810.

As indicated in FIG. 12, projections 824 may taper in a radial direction toward central channel 815 to provide a more circular cross-sectional shape for channels 811-814, although projections 824 could have other shapes, such as a uniform thickness. Although four twisting channels 811-814 are depicted in the exemplary embodiment of FIG. 12, other numbers of channels may be present, such as by using more or fewer projections. Further, although projections 824 may be equally spaced about inner piece 810 to provide equally sized channels 811-814, projections may be unequally spaced so that the resulting channels vary in size.

Figure 13:
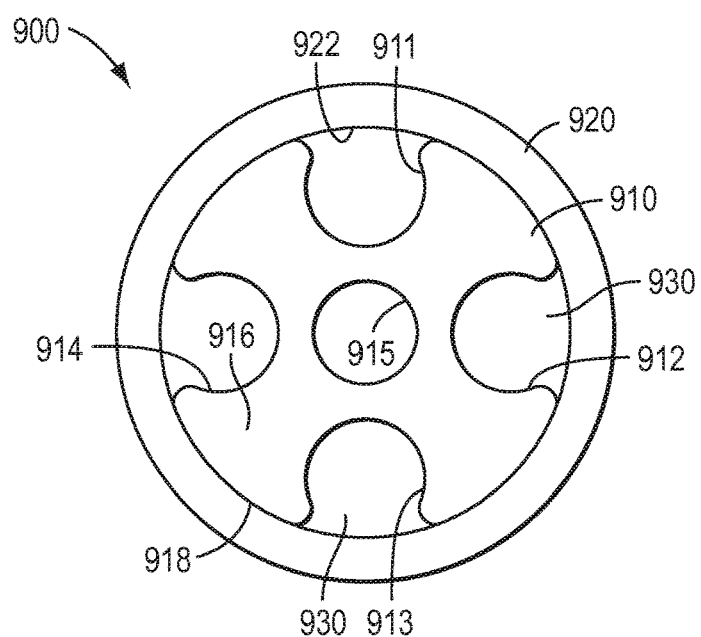
FIG. 13 is an end view of an actuation element guide, according to yet another exemplary embodiment.

Turning to FIG. 13, an end view is shown of another exemplary embodiment of an actuation element guide 900. According to an exemplary embodiment, actuation element guide 900 includes an inner piece 910 and an outer piece 920, which may be referred to as first and second pieces. As shown in FIG. 13, outer piece 920 has a simple tube structure that surrounds inner piece 910. For instance, outer piece 920 is a tube with a generally cylindrical cross-section having a generally uniform wall thickness. As a result, outer piece 920 may be manufactured via a fairly straightforward extrusion technique, although other techniques may be used. Inner piece 910 forms a non-twisting central channel 915, according to an exemplary embodiment.

According to an exemplary embodiment, outer surface 912 of inner piece 910 defines projections 916 that extend radially outward from central channel 915. Outer surface 912 may also define open regions 930 between projections 916, as shown in the exemplary embodiment of FIG. 13. According to an exemplary embodiment, projections 916 and open regions 930 define a spoke-like configuration for inner piece 910. Projections 916 and open regions 930 twist about central channel 915 along an axial direction of guide 900 (e.g., into and out of the page of FIG. 13, similar to the exemplary embodiment of FIG. 11), according to an exemplary embodiment. Thus, inner piece 910 and outer piece 920 may cooperate with one another, such as via ends 918 of projections 916 contacting an inner surface 922 of outer piece 920, so that projection 916, open regions 930, and inner surface 922 define twisting channels 911-914 of guide 900. As a result, inner piece 910 and outer piece 920 may define twisting channels 911-914 at a point (e.g., cross-section) along the axial length of guide 900. According to an exemplary embodiment, a cross section of the twisting channels 911-914 taken at a location along the axial length of guide 900 (e.g., transverse to a longitudinal axis of actuation element guide 900) includes surface portions of both the inner piece 910 and the outer piece 920, in particular, an interior surface portion of outer piece 920 and an exterior surface portion of inner piece 910.

Projections of an actuation element guide may vary in width along a radial direction of the guide. As shown in the exemplary embodiment of FIG. 13, projections 916 increase in width in a radial direction from central channel 915 to outer piece 920, such as to provide channels 911-914 with approximately circular cross-sections. Thus, projections 916 may have flared outer radial ends, as shown in the exemplary embodiment of FIG. 13. However, projections 916 may have other shapes, such as a uniform width along the radial direction from central channel 915 to outer piece 920. Spaces defined by adjacent projections 924 and inner wall 922 of outer piece 920 define twisting channels 911-914. However, more or fewer channels may be defined in actuation element guide 900 by using more or fewer projections 916. Further, although projections 916 may be equally spaced about central channel 915 to form equally sized channels 911-914, as indicated in FIG. 13, projections may instead vary in spacing to provide channels that vary in size.

Figure 14:
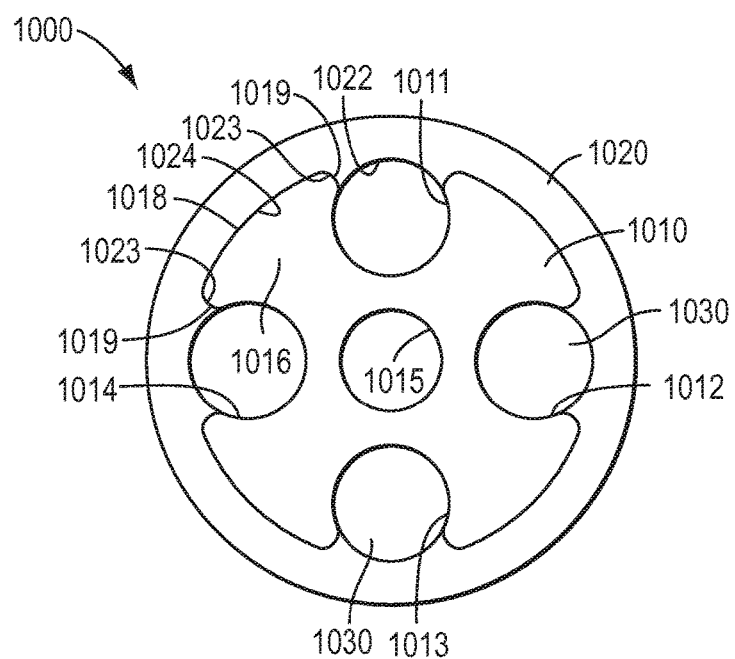
FIG. 14 is an end view of an actuation element guide, according to another exemplary embodiment.

FIG. 14 is an end view of an actuation element guide 1000 that includes an inner piece 1010 and an outer piece 1020, according to another exemplary embodiment. Outer piece 1020 surrounds inner piece 1010, similar to outer piece 920 and inner piece of the exemplary embodiment of FIG. 13, except that outer piece 1020 in the exemplary embodiment of FIG. 14 includes an inner wall 1022 shaped to mate with outer radial ends 1018 of projections 1016 of the inner piece 1010, according to an exemplary embodiment. For example, inner wall 1022 of outer piece 1020 includes recesses 1024 to each receive outer radial ends 1018 of projections 1016. Inner wall 1022 may further include protrusions 1023 located at lateral sides of recesses 1024 that conform inner wall 1022 to a shape of projections 1016. Corresponding recesses 1024 may be formed into inner wall 1022 of outer piece 1020 or be formed by protrusions 1023 of inner wall 1022. Inner piece 1010 further forms a non-twisting central channel 1015.

Inner piece 1010 and outer piece 1020 may cooperate to define twisting channels, such as, for example, via projections 1016, open regions 1030, and inner wall 1022 of outer piece 1020 cooperating to define twisting channels 1011-1014. As a result, inner piece 1010 and outer piece 1020 define twisting channels 1011-1014 at a point (e.g., cross-section) along the axial length of guide 1000, according to an exemplary embodiment. According to an exemplary embodiment, a cross section of the twisting channels 1011-1014 taken at a location along the axial length of guide 1000 (e.g., transverse to a longitudinal axis of actuation element guide 1000) includes surface portions of both the inner piece 1010 and the outer piece 1020, in particular, an interior surface portion of outer piece 1020 and an exterior surface portion of inner piece 1010. Further, four twisting channels 1011-1014 are depicted in the exemplary embodiment of FIG. 14, other numbers of channels may be present, such as by using more or fewer projections. In addition, although projections 1016 may be equally spaced about inner piece 1010 to provide equally sized channels 1011-1014, projections may be unequally spaced so that the resulting channels vary in size.

Figure 15:
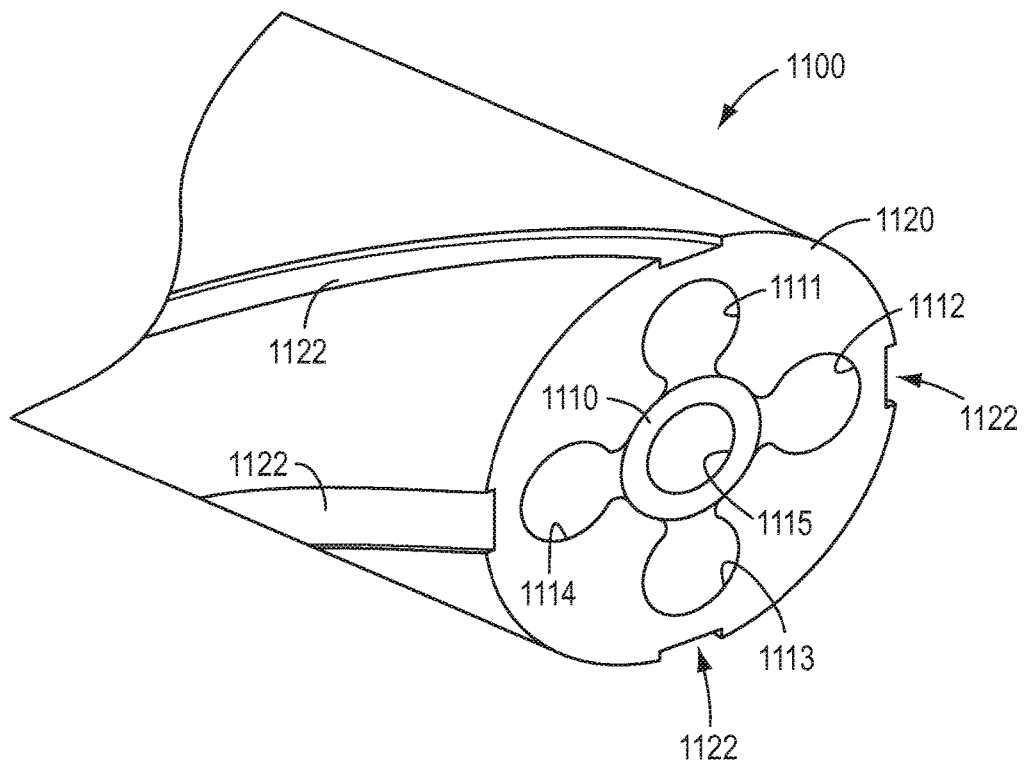
FIG. 15 is an end view of an actuation element guide, according to another exemplary embodiment.

As depicted in the exemplary embodiments of FIGS. 8-11 and 14-18, channels of an actuation element guide may have a generally circular cross-sectional shape. However, actuation element guides and channels of the various actuation element guide embodiments described herein may have other shapes. For instance, a cross-sectional shape of a guide or one or more channels of a guide may be modified to affect the bending strength of an actuation element guide. Turning to FIG. 15, another exemplary embodiment of an actuation element guide 1100 is shown. Actuation element guide 1100 includes an inner piece 1110 and an outer piece 1120 (e.g., first and second pieces). Inner piece 1110 defines a non-twisted central channel 1115 and inner piece 1110 and outer piece 1120 cooperate to define twisted channels 1111-1114 according to any of the various exemplary embodiments described herein.

According to an exemplary embodiment, outer piece 1120 may include one or more cutouts 1122 to enhance the flexibility of actuation element guide 1100, as shown in the exemplary embodiment of FIG. 15. Cutouts 1122 may be located, for example, along a longitudinal length of actuation element guide 1100 corresponding to locations experiencing bending (i.e., locations where enhanced flexibility of guide 1100 may be advantageous), such as, for example, locations corresponding to a wrist of an instrument. According to an exemplary embodiment, cutouts 1122 are disposed in guide 1100 in locations corresponding to the greatest regions of bending of a wrist. Cutouts 1122 may include other shapes than the generally rectangular cutout shape shown in the exemplary embodiment of FIG. 15, such as, for example, square, oval, arcuate, or other shapes familiar to one of ordinary skill in the art.

Figure 16:
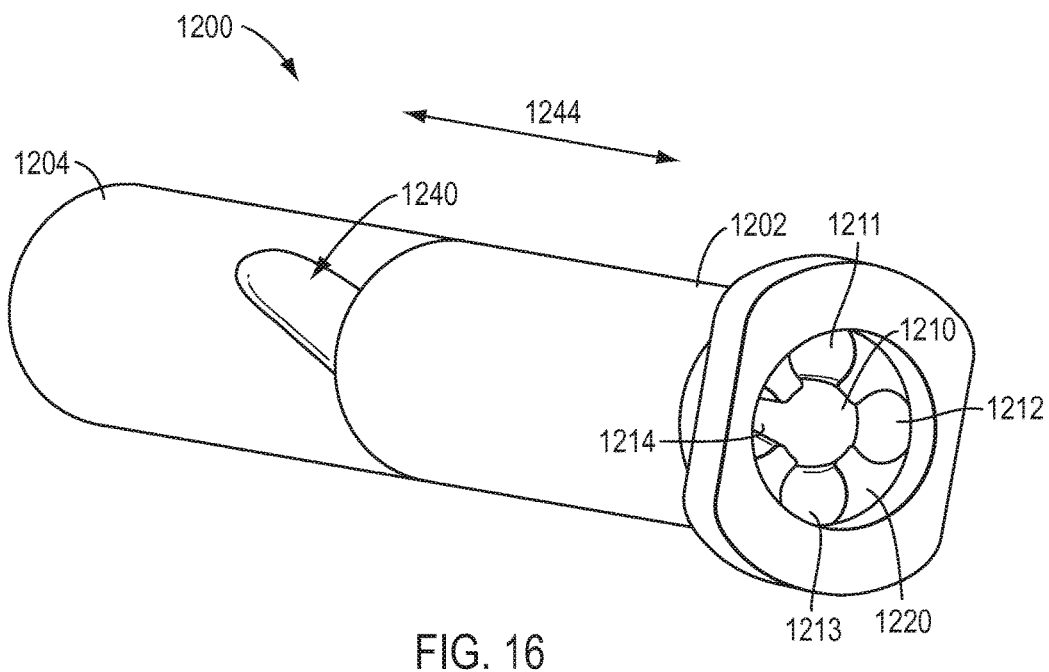
FIG. 16 is a perspective view of an actuation element guide including port openings, according to an exemplary embodiment.

Turning to FIG. 16, an exemplary embodiment of an actuation element guide 1200 is shown that includes an inner piece 1210 and an outer piece 1220 (e.g., first and second pieces). Inner piece 1210 and outer piece 1220 may be configured according to any of the various exemplary embodiments described herein and cooperate to define twisted channels 1211-1214. According to an exemplary embodiment, a cross section of the twisting channels 1211-1214 taken at a location along the axial length of guide 1200 (e.g., transverse to a longitudinal axis of actuation element guide 1200) includes surface portions of both the inner piece 1210 and the outer piece 1220, in particular, an interior surface portion of outer piece 1220 and an exterior surface portion of inner piece 1210. According to an exemplary embodiment, twisted channels 1211-1214 are twisted along the entire axial length of guide 1200 (e.g., along axial direction indicated by arrows 1244). According to another exemplary embodiment, guide 1200 includes a first section 1202 in which channels 1211-1214 are twisted (as described in the various exemplary embodiments herein) and a second section 1204 in which channels 1211-1214 are straight along the axial direction of guide 1200.

In the exemplary embodiment of FIG. 16, at least one of channels 1211-1214 includes a port opening 1240 that provides access to the at least one channel from an exterior of guide 1200. Channels 1211-1214 may be selected to include a port opening 1240 based upon what extends through channels 1211-1214. For example, actuation elements (not shown) extend through channels 1211, and 1213 and conduits (not shown), such as electrical energy conduits, extend through channels 1212 and 1214, which each include a port opening 1240. As result, the actuation elements are supported by channels 211 and 213 along the axial length of guide 1200 and the conduits are supported by channels 212 and 214 in a distal portion of guide 1200, but the conduits may exit guide 1200 via port openings 1240 towards a proximal portion of guide 1200. As indicated in the exemplary embodiment of FIG. 16, ports 1240 may taper and decrease in depth along the axial direction 1244.

Figure 17:
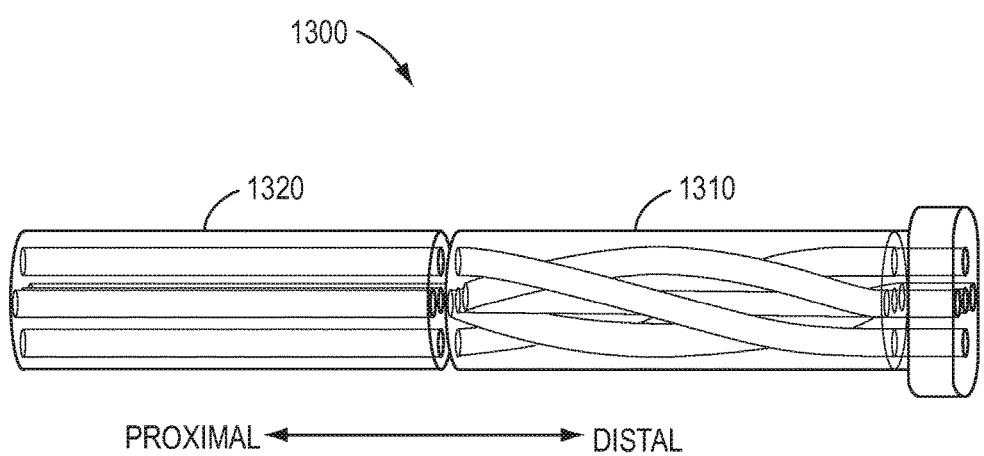
FIG. 17 is a side view of an actuation element guide comprising a plurality of portions along a proximal-distal direction, according to an exemplary embodiment.

As described in the exemplary embodiments herein, an actuation element guide may include a plurality of pieces disposed generally concentrically relative to a central channel of the guide. Actuation element guides also may include a plurality of pieces along a longitudinal direction of the actuation element guide. Turning to FIG. 17, an exemplary embodiment of an actuation element guide 1300 is depicted that includes a first portion 1310 and a second portion 1320, with first portion 1310 and second portion 1320 being aligned in series (e.g., end to end) along the longitudinal direction of guide 1300. Second portion 1320 may be formed as a single piece, with straight, non-twisted channels. Because second portion 1320 includes straight channels, second portion 1320 may be manufactured via, for example, extrusion without twisting second portion 1320. As a result, manufacture of guide 1300 can be facilitated. According to an exemplary embodiment, second portion 1320 may be positioned in a shaft of an instrument (e.g., shaft 222 of FIG. 2) so that second portion 1320 does not substantially bend. As a result, straight channels may be provided in section portion 1320, which facilitates its manufacture.

First portion 1310 may include twisted channels and be formed from multiple pieces, such as according to the various actuation element guide embodiments described herein. First portion 1310 may be positioned within a wrist of an instrument (e.g., wrist 230 of FIG. 2) so that first portion 1310 is bent but actuation elements extending through the twisted channels of first portion 1310 do not substantially change in path length. However, first portion 1310 may be shorter in length along the proximal-distal direction of guide 1300 than the various actuation element guide embodiments described herein, which facilitates manufacture of first portion 1310 due to its short length over which its channels twist, in accordance with various exemplary embodiments. The channels of first portion 1310 and second portion 1320 align with one another where first portion 1310 and second portion 1320 interface so any actuation elements, conduits, or other instrument components extending through the channels extend through both first portion 1310 and second portion 1320, according to an exemplary embodiment.

According to an exemplary embodiment, first portion 1310 and second portion 1320 are joined to one another, such as via, for example, welding, adhesive bonding, or another joining process familiar to one of ordinary skill in the art. According to another exemplary embodiment, first portion 1310 and second portion 1320 are not joined to one another but are connected via components extending through the respective channels of first portion 1310 and second portion 1320, such as actuation elements. According to another embodiment, the positions of first portion 1310 and second portion 1320 are reversed relative to the proximal-distal direction, with first portion 1310 located at a distal end of guide 1300 and second portion 1320 located at a proximal end of guide 1300. Further, although the exemplary embodiment of FIG. 17 has been described with first portion 1310 and second portion 1320 each being a single piece, first portion 1310 and/or second portion 1320 may be formed by a plurality of pieces joined together.

Figure 18:
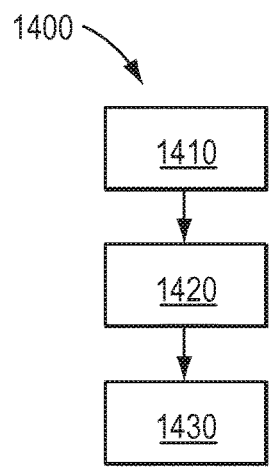
FIG. 18 is a flow chart of a manufacturing process for an actuation element guide, according to an exemplary embodiment.

Pieces of actuation element guides of the various exemplary embodiments described herein may be manufactured via various techniques. According to an exemplary embodiment, inner and outer pieces of an actuation element guide are manufactured via, for example, molding, extrusion, and other techniques. Turning to FIG. 18, a flow diagram for an exemplary method of manufacturing an actuation element guide is shown. The method 1400 of FIG. 18 may be used to manufacture the actuation element guides of the various exemplary embodiments described herein. In step 1410, the pieces of the actuation element guide are manufactured as separate components. For example, inner and outer pieces of an actuation element guide are each manufactured via molding, extrusion, or other techniques. In step 1420, the pieces of the actuation element guide (e.g., the inner and outer pieces) are assembled together. In step 1430, the pieces of the actuation element guide are joined to one another such as, for example, via welding (e.g., laser welding, friction welding, or other types of welding processes), adhesive bonding, or other techniques. However, the various exemplary embodiments described herein are not limited to joining the pieces to one another because the pieces of an actuation element guide may be assembled together without joining (e.g., fixing) the pieces to one another.

Figure 19:
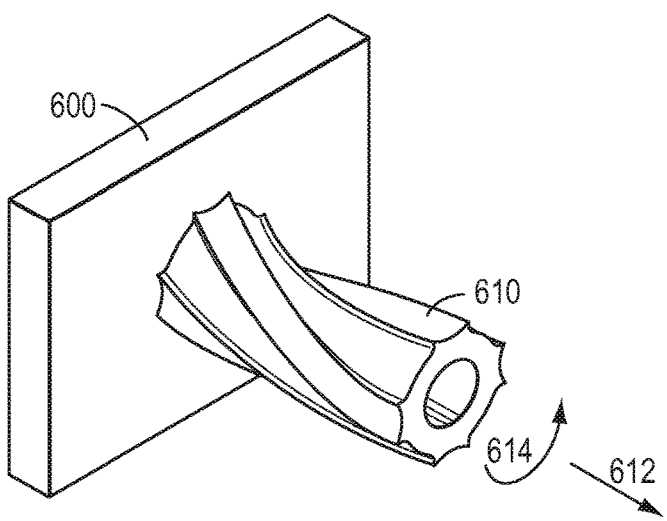
FIG. 19 is a perspective view of an extrusion process for manufacturing an inner piece of an actuation element guide, according to an exemplary embodiment.

One technique of manufacturing an actuation element guide piece is extrusion. Turning to FIG. 19, an extrusion technique is shown for manufacturing an inner piece 610 of an actuation element guide, according to an exemplary embodiment. As shown in the exemplary embodiment of FIG. 19, inner piece 610 is formed by forcing material through an extrusion die 600 along the direction indicated by arrow 612. A twisted shape may be imparted to inner piece 610, such as along the direction indicated by arrow 614, by extruding inner piece 610 as a straight piece and then heat forming the extrusion in a subsequent step to impart the twist to inner piece 610. Inner piece 610 may have the configuration of the exemplary embodiment of FIGS. 8-11, as indicated in FIG. 19, or inner piece 610 may have the configuration of any of the various exemplary embodiments of actuation element guide inner pieces described herein. Further, although inner piece 610 has been described as being manufactured by an extrusion technique, inner piece 610 may be manufactured in another way, including via molding, for example.

Figure 20:
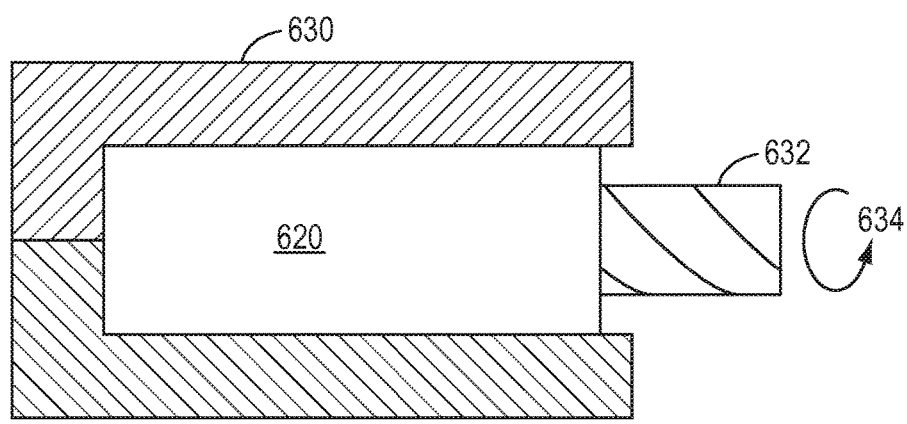
FIG. 20 is a cross-sectional view of a molding process for manufacturing an outer piece of an actuation element guide, according to an exemplary embodiment.

Another exemplary technique for manufacturing a piece of an actuation element guide is molding. With reference to FIG. 20, for example, a side cross-sectional view is shown of a molding process for manufacturing an outer piece 620 of an actuation element guide, according to an exemplary embodiment. Outer piece 620 may be formed by supplying molten material into mold 630, which solidifies into shape desired for outer piece 620, as defined by mold 630 and an insert 632 provided within mold 630. Insert 632 may have a cross-sectional shape corresponding to inner surface 522 of the exemplary embodiment of FIG. 10, or the inner surface of other outer pieces described in the various exemplary embodiments herein, with insert 632 being twisted along its longitudinal length to impart a twisted shape to the inner surface of outer piece 620. Once molding is complete, insert 632 may be removed by twisting and pulling insert 632 from outer piece 620, such as along the direction indicated by arrow 634 in FIG. 20, and then outer piece 620 may be removed from mold 630. Outer piece 620 may have the configuration of the exemplary embodiment of outer piece 520 FIGS. 8-10, or outer piece 620 may have the configuration of any of the various exemplary embodiments of actuation element guide outer pieces described herein. Further, although outer piece 620 has been described as being manufactured by a molding process, outer piece 620 may be manufactured by other processes, including extrusion, for example.

Actuation element guide pieces of the various exemplary embodiments described herein may be made from a flexible material. According to an exemplary embodiment, actuation element guide pieces are made of, for example, a flexible plastic, such as, for example, an elastomer, a polyether block amide (e.g., PEBAX®), fluorinated ethylene propylene (FEP), and other flexible plastics familiar to one of ordinary skill in the art. According to an exemplary embodiment, the inner and outer pieces of an actuation element guide are made of the same material. According to another exemplary embodiment, the inner and outer pieces of an actuation element guide are made of different materials. For example, an inner piece are made of a harder material than the outer piece, so as to provide higher wear resistance for the inner piece because the inner piece may experience more wear than the outer piece of an actuation element guide. Moreover, the inner piece is closer to the neutral axis of an actuation element guide, so using a higher hardness or higher strength material has less effect on the bending properties of an actuation element guide than using the same material for the outer piece. For example, an inner piece of an actuation element guide is made of material having a hardness of, for example, about 72 durometer Shore D. The outer piece of an actuation element guide is made of, for example, a material having a hardness ranging from, for example, about 55 durometer to about 75 durometer Shore D.

Figure 21:
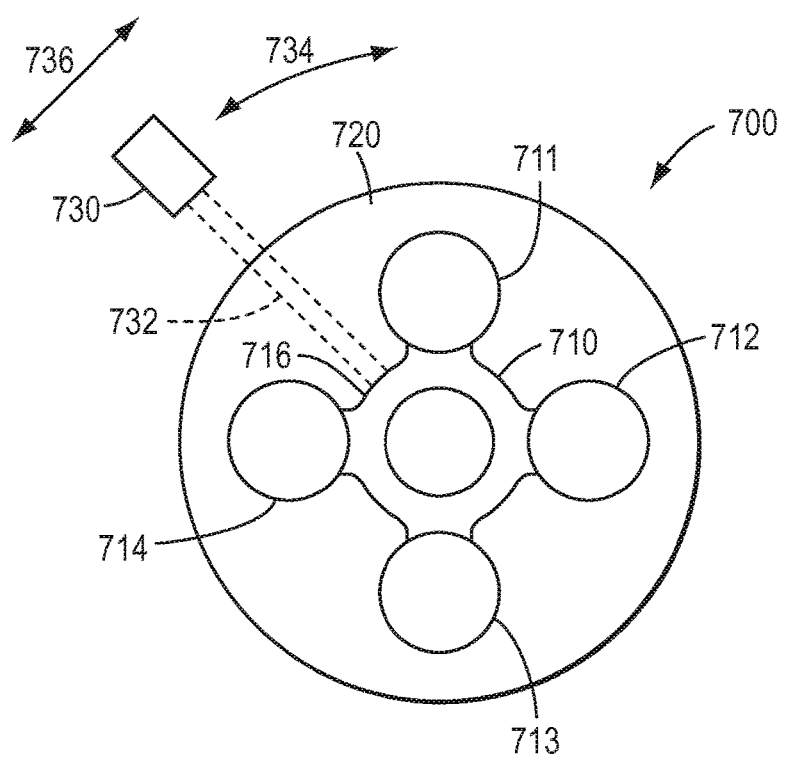
FIG. 21 is a cross-sectional view of a laser welding process for manufacturing an actuation element guide, according to an exemplary embodiment.

Once the inner and outer pieces have been manufactured, the inner and outer pieces may be joined together to form an actuation element guide. According to an exemplary embodiment, inner and outer pieces of an actuation element guide are joined together via laser welding. Turning to FIG. 21, a laser welding process is depicted that illustrates joining an inner piece 710 and an outer piece 720 to form an actuation element guide 700, according to an exemplary embodiment. Although inner piece 710 and outer piece 720 are configured according to the exemplary embodiment of FIGS. 8-11, the laser welding process of the exemplary embodiment of FIG. 21 may be applied to the various actuation element guide embodiments described herein.

As shown in FIG. 21, a laser source 730 emits a laser beam 732 that is directed to an outer surface 716 of inner piece 710. According to an exemplary embodiment, outer piece 720 may be substantially transparent or translucent and configured for transmission of laser beam 732 or a majority of laser beam 732 to pass through outer piece 720 until beam 732 reaches the outer surface 716 of inner piece 710, which may be colored or otherwise configured to absorb the laser beam 732. As a result, beam 732 may heat inner piece 710 at its outer surface 716, which results in the inner piece 710 being welded to outer piece 720.

A weld formed by laser welding may be a continuous weld along the longitudinal length of an actuation element guide or guide pieces may be welded together via discrete welds in a non-continuous manner. A weld between inner piece 710 and outer piece 720 may be a circumferential weld, such as by moving laser source 730 about outer piece 720 in at least one of the directions indicated by arrow 734 in FIG. 21 or by moving inner piece 710 and outer piece in at least one of the directions indicated by arrow 734. According to another exemplary embodiment, beam 732 has a linear or planar shape (e.g., have a length along directions 736 in FIG. 12) and pieces 710, 720 and beam 732 are moved relative to one another, such as to move pieces 710, 720 or beam 732 into or out of the page of FIG. 21. According to another exemplary embodiment, beam 732 surrounds pieces 710, 720 (e.g., beam 732 is an annular or circular beam) so that a relative rotation between beam 732 and pieces 710, 720 along directions 734 may be minimized or avoided.

Techniques other than laser welding can be used to join pieces of an actuation element guide. According to an exemplary embodiment, pieces of an actuation element guide are joined, for example, via adhesive bonding, friction fitting, heat shrinking, or other joining techniques. For example, an outer piece may be heated to expand the outer piece, after which the outer piece may be fitted over an inner piece, and then allowed to cool so the outer piece may shrink and be force fit onto the inner piece. In another example, inner and outer pieces may be joined by making the outer piece out of heat shrinkable material, placing the outer piece about the inner piece, and heat shrinking the outer piece to assemble an actuation element guide. One consideration when joining inner and outer pieces to manufacture an actuation element guide is that the pieces remain joined in a substantially fixed position to one another during subsequent use, including movement of actuation elements relative to and against an actuation element guide and cleaning of an actuation element guide, which can include flushing fluid through an actuation element guide at a relatively high pressure. Further, although the exemplary embodiments of actuation element guides described herein may include a first piece and a second piece, such as an inner piece and an outer piece, the actuation element guides may include more than two pieces, such as, for example, three, four, or more pieces having surfaces that cooperate to define a twisting channel. In addition, the various pieces of the actuation element guides of the exemplary embodiments described herein may be joined to one another or may be placed in contact with one another without joining (e.g., fixing) the pieces to one another.

A process of joining first and second pieces to one another may result in an alteration of the geometry of at least one of the first and second pieces. As shown in the exemplary embodiment of FIG. 12, an inner piece 810 may be inserted within an outer piece 820, with inner piece 810 having a tube structure. Inner piece 810 and outer piece 820 may be subsequently joined to one another, such as via the various welding exemplary embodiments described herein. The joining process, such as heat from a welding process, may result in alteration of the geometry of at least one of inner piece 810 and outer piece 820. For example, portions of inner piece 810 may melt and flow, resulting in alteration of the geometry of the inner piece. According to an exemplary embodiment, the joining process may result in the inner piece having the geometry of inner piece 510 depicted in the exemplary embodiment of FIG. 9. For instance, portions of the inner piece may flow radial outward to form an outer surface 517 that includes raised portions 518 and grooves 519, as shown in the exemplary embodiment of FIG. 9.

The exemplary embodiments and methods described herein have been described as being utilized with surgical instruments for teleoperated surgical systems. However, the exemplary embodiments and methods described herein may be used with other surgical devices, such as laparoscopic instruments and other hand held instruments. Further, the exemplary embodiments and methods may be employed in other application that use remotely actuatable wrist or multiple joint structures, such as to remotely position an object attached to the wrist or joint structures. For instance, the exemplary embodiments described herein may be used in devices used for pipe inspection and other devices utilizing remote access via teleoperation or manual actuation.

By providing an actuation element guide comprising a plurality of pieces, manufacture of the actuation element guide may be facilitated, while providing an actuation element guide that supports actuation elements along a twisted path to substantially prevent a change in path length of the actuation elements.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled to their full breadth and scope, including equivalents.

What is claimed is:

1. An actuation element guide for a surgical instrument, the actuation element guide comprising:
   a first piece made of a first flexible polymer material;
   a second piece made of a second flexible polymer material; and
   at least one guide channel sized to receive an actuation element of a surgical instrument, the at least one guide channel defining a twisted path about a longitudinal centerline of the actuation element guide;
   wherein a cross-section of the at least one guide channel, at a location along an axial length of the actuation element guide, is defined by a surface portion of the first piece and by a surface portion of the second piece.

2. The actuation element guide of claim 1: wherein one of the first piece and the second piece comprises radially extending projections;
   wherein the radially extending projections twist about the longitudinal centerline of the actuation element guide; and
   wherein the at least one guide channel comprises a plurality of guide channels defined at least in part by the projections.

3. The actuation element guide of claim 2, wherein the radially extending projections have a spoke-like configuration.

4. The actuation element guide of claim 2, wherein the first piece and the second piece are concentrically disposed relative to each other.

5. The actuation element guide of claim 2: wherein the second piece surrounds the first piece, and
   wherein the second piece comprises the radially extending projections, the radially extending projections extending radially inward from the second piece and into contact with the first piece.

6. The actuation element guide of claim 5, wherein an outer surface of the first piece comprises grooves to receive ends of the projections.

7. The actuation element guide of claim 5, wherein the first piece is a cylindrical tube.

8. The actuation element guide of claim 2:
   wherein the second piece surrounds the first piece; and
   wherein the first piece comprises the radially extending projections, the radially extending projections extending radially outward from the first piece and into contact with the second piece.

9. The actuation element guide of claim 8, wherein an inner surface of the second piece comprises grooves to receive ends of the radially extending projections.

10. The actuation element guide of claim 8, wherein the second piece is a cylindrical tube.

11. The actuation element guide of claim 1, wherein the first piece and the second piece are separate pieces joined to one another.

12. The actuation element guide of claim 1, further comprising an outer lateral surface and a recess located in the outer lateral surface, the outer lateral surface being on one of the first and second pieces.

13. The actuation element guide of claim 1, wherein the first flexible polymer material is harder than the second flexible polymer material.

14. The actuation element guide of claim 1, further comprising a first portion and a second portion disposed longitudinally and end-to-end with each other.

15. The actuation element guide of claim 14, wherein the second portion comprises longitudinally straight guide channels and the first portion comprises the first piece and the second piece.

16. The actuation element guide of claim 1, wherein the at least one guide channel is radially offset from the longitudinal centerline of the actuation element guide.

17. The actuation element guide of claim 1, further comprising:
    a lateral side wall; and
    at least one port opening disposed in the lateral side wall;
    wherein the at least one port opening leads to an interior region of the actuation element guide.

18. A medical device comprising:
    a shaft comprising a distal end;
    a surgical end effector comprising a movable component;
    a flexible actuation element guide positioned between the distal end of the shaft and the surgical end effector, the actuation element guide comprising:
    a guide channel located between an inner piece and an outer piece, the guide channel twisting around a longitudinal centerline of the actuation element guide; and
    an actuation element comprising a distal end, the actuation element extending through the guide channel, the distal end of the actuation element being mechanically coupled to the movable component of the end effector.

19. The medical device of claim 18, further comprising:
    a wrist mechanism comprising a first end, a second end opposite the first end, and one or more rotational joints, the first end of the wrist mechanism being mechanically coupled to the distal end of the shaft, the second end of the wrist mechanism being mechanically coupled to the surgical end effector, the actuation element guide extending through the wrist mechanism.

20. The medical device of claim 19, wherein the guide channel of the actuation element guide extends through the wrist mechanism.

21. The medical device of claim 18, wherein the guide channel between the inner piece and the outer piece comprises a first guide channel and a second guide channel.

22. The medical device of claim 21, wherein the first guide channel and the second guide channel twist around the longitudinal centerline of the actuation element guide.

23. The medical device of claim 18, wherein the movable component of the surgical end effector comprises a cutting blade.

24. The medical device of claim 19, wherein the actuation element guide is configured to conserve a length of an actuation element during bending of the one or more rotational joints of the wrist mechanism.

* * * * *